United States Patent [19]

Mahal

[11] Patent Number: 4,479,989
[45] Date of Patent: Oct. 30, 1984

[54] FLEXIBLE CONTAINER MATERIAL

[75] Inventor: Mohan S. Mahal, Pleasant Hill, Calif.

[73] Assignee: Cutter Laboratories, Inc., Berkeley, Calif.

[21] Appl. No.: 446,303

[22] Filed: Dec. 2, 1982

[51] Int. Cl.³ .......................... B32B 1/02; B65D 65/38
[52] U.S. Cl. ........................................ 428/35; 525/98; 604/408; 604/415
[58] Field of Search ................... 525/98; 604/408, 415; 428/35

[56] References Cited

U.S. PATENT DOCUMENTS

| | | | |
|---|---|---|---|
| 3,595,942 | 7/1971 | Wald | 525/339 |
| 3,921,630 | 11/1975 | McPhee | 215/231 |
| 4,100,953 | 7/1978 | Miller | 383/14 |
| 4,178,328 | 11/1979 | Thiruvillakkat | 525/98 |
| 4,350,795 | 9/1982 | Bohm et al. | 525/98 |

*Primary Examiner*—John E. Kittle
*Attorney, Agent, or Firm*—David J. Aston

[57] ABSTRACT

Film material for use in sterilized medical solution containers such as blood bags or I.V. bags, comprising 30–90% linear low density polyethylene (LLDPE) and 10–70% styrene-ethylene-butylene-styrene (SEBS). The particular LLDPE and SEBS materials are selected from among known LLDPE and SEBS materials according to density, in the case of LLDPE, and styrene/rubber ratio and composition in the case of SEBS. Up to 10% of an optional third component such as high melt index LLDPE or polypropylene may be added as a processing aid. Material having greater than 50% LLDPE is particularly well suited for medical solution container application.

14 Claims, 3 Drawing Figures

FLEXIBLE CONTAINER MATERIAL

BACKGROUND OF THE INVENTION

1. Field of the Invention

The present invention relates to plastic containers for medical fluids such as intravenous solutions and blood, and more particularly, to a fabricated film container having a novel film material.

2. Prior Art

A number of film materials are known for use in medical fluid containers. A widely used material in the past has been polyvinyl chloride, which is used at the present time in blood bags and in commercially available flexible intravenous solution containers. Polyvinyl chloride, however, is disadvantageous in that it is often formulated so as to be brittle at low temperatures and to contain plasticizers which may be extracted by certain intravenous solutions.

Several polyolefins are also known for application in the field of medical containers, particularly in semi-rigid containers, with rigid shoulder and/or base portions, which assume a free-standing shape and collapse upon withdrawal of the container's contents. This design eliminates the need for an air inlet in such containers, an important advantage of flexible medical fluid containers generally. See for example, U.S. Pat. No. 3,921,630, which discloses a propylene-ethylene copolymer and U.S. Pat. No. 4,100,953, which suggests that medium and high density polyethylene may be used for such containers. In fact, at the present, most semi-rigid containers are currently made from propylene/ethylene copolymers. U.S. Pat. No. 4,140,162 suggests various propylene/styrene-ethylene-butylene-styrene (SEBS) blends for a blow-molded oval container with more flexibility. It is often desirable, however, that the container be in a flexible bag form to enable flat shipment of empty containers and more convenient storage.

Another type of medical fluid container, known to be used outside the United States, is a flexible laminate container, such as described in U.K. No. 2,040,263A. This film bag comprises a three layer laminate consisting of a propylene outer layer, a polyamide middle layer, and an ethylene/butylene inner layer. U.S. Pat. No. 4,210,686 discloses a polyolefin/SEBS blend as one layer of a laminate, with a polyolefin outer layer. The polyolefins are derived from propylene, ethylene, and 4-methylpentene-1. The laminate approach generally employs a rubbery material for softness and a high temperature material such as polypropylene or high- or medium-density polyethylene to permit very high temperature resistance during sterilization. A drawback to the laminate approach, however, is that scrap materials from the manufacture of such films cannot be reground into feedstock for the film-making equipment.

Prior art sterilization plastic containers have heretofore been constructed of film or flexible materials having a crystalline melting point (MP) in the range of 130° to 165° C. in order that they may be heat sterilized without intolerable distortion. Thus, polypropylene, with copolymers or blends, with MP's in the range 165° C. have been commonly used. They have been described for use with SEBS having a melting point around 120° C. On the other hand, polyethylenes (MP 109° C. to 125° C.) have been used in small amounts, if at all, as softening agents. Polypropylene, however, is undesirable in that it may not be irradiated as, for instance, in radiation sterilization and in that it becomes brittle at low temperatures (around 0° C.) and in that it is inherently stiff, and will spring back to its molded shape.

It is therefore among the objects of the present invention to provide a medical fluid container which has a flexible film body for flat storage and collapse, together with good low temperature flexibility in the film body, sufficient temperature resistance to softening and/or melting during steam sterilization, and capability for radiation sterilization. Other objects of the present invention, which will become apparent from the following description include providing a container of film material which has superior optical clarity and a combination of flexibility and strength which impart superior handling characteristics over a wide temperature range.

SUMMARY OF THE INVENTION

The foregoing and other objects are accomplished by a container having a flexible film body formed from a novel polymeric blend which provides superior handling characteristics and optical clarity. The blend of the present invention is based, in general terms, on the discovery that a high melting point olefin such as polypropylene or medium- or high-density polyolefin is not necessary to produce an olefin blend which may be sterilized at high temperatures without intolerable distortion. A low melting point low density polyethylene may be used as a first component provided that a second component of an elastomeric material is added which will provide shaped-retaining properties.

The blend contains a first component of 30–90%, preferably 50–80%, linear low density polyethylene (LLDPE) having a density less than 0.940 g/cm$^3$, preferably 0.918–0.935. Linear low density polyethylene (LLDPE) refers to a particular type of low density polyethylene wherein there is an absence of long chain branching. The LLDPE is selected to impart strength and flexibility.

The blend further contains a second component of 10–70%, preferably 20–50% of an elastomeric material, preferably an SEBS block copolymer wherein the styrene comprises no more than 35% of the block copolymer. The SEBS is selected to impart strength and flexibility. It may be characterized as being substantially free of plasticizer and having a relatively high percent elongation, preferably greater than 500.

The materials of the present invention further contemplate the addition of 1–10% of a high melt index (MI) material for improved processing properties, such as polypropylene/polyethylene and LLDPE having an MI of 5–50.

The final blend may be autoclaved, handles exceptionally well in drop testing, has excellent low temperature properties, and may be radiation sterilized.

One aspect of the present invention is the use of LLDPE as a major (i.e. 50% or more) component.

DESCRIPTION OF THE PREFERRED EMBODIMENT

Figure 1:
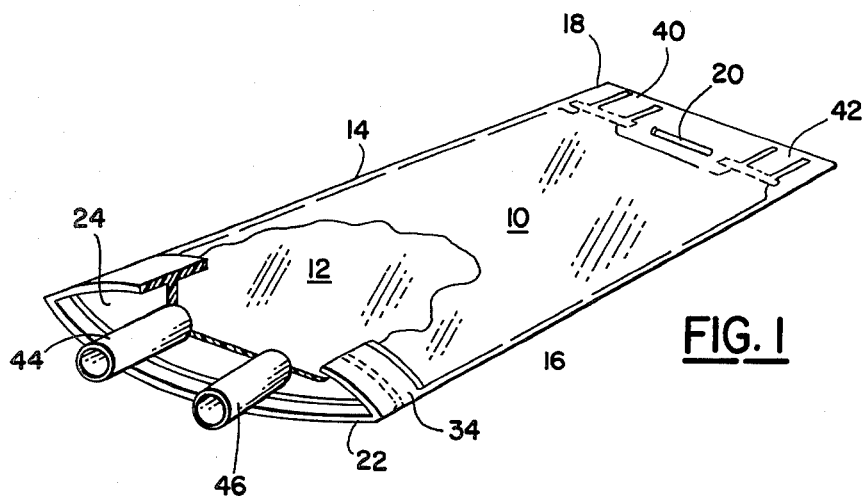
FIG. 1 is a perspective breakaway view of a medical solution container in accordance with the present invention.

For purposes of describing the method of making and using the present invention in clear, complete, and concise terms, a number of general principles, followed by specific examples are set forth hereinafter, so that the invention defined by the appended claims may be practiced by one of ordinary skill in the art.

SELECTION OF MATERIALS

The first component of the present blend is a linear low density polyethylene, defined generally in the polymer art and in this specification as a commercially prepared polyethylene which may contain up to 5% vinyl acetate units, up to 8% propylene units, or up to 6% $C_4$-$C_8$ units. The linear low polyethylene is selected on the basis a density of less density than 0.940 g/cm$^3$, a melting point of less than 125° C., and a Vicat Softening Point of 90°-110° C., a flexural modulus of 30-100K psi, and a melt index of 0.1-5.

A critical feature of the present invention is the use of "linear low density polyethylene" (LLDPE). This term is used herein in the sense that it is generally used in the industry, and more specifically, in the sense that it refers to polyethylene with a basically linear chain structure of having short (1-C) chain branching of 10-30/1000C and having an absence of long chain branching, i.e. less than 30 side chains greater than 6C per molecule. Such material is defined herein as having a density less than 0.940 g/cm$^3$, as distinguished from high density polyethylene and a crystalline melting point in excess of 120° C., as distinguished from melting points which are typical of branched chain low density polyethylene.

The LLDPE of the present invention may be further characterized and selected from LLDPE's on the basis of its relatively high molecular weight and narrow molecular weight distribution band. This is indicated by its relatively low melt index, g/10 min., which will be in the range of 0.1 to 5, preferably 1 to 3. This material can be readily extruded or blown into film and will produce a blend which produces a film according to the present invention which is high in tensile, drop, and impact strength.

The present LLDPE may be further characterized and selected from LLDPE's on the basis of a moderate degree of crystallinity. This is indicated by its high Vicat Softening Point, greater than 90° C., which produces a blend which can be heat sterilized. Crystallinity is also indicated by a relatively low flexural modulus in LLDPE's of the present blend, on the order of 30K psi-100K psi. This produces an air independent, very flexible, collapsible bag which feels limp.

Finally the present LLDPE may be characterized and selected from LLDPE's on the basis of clarity which this component imparts to the blend film, which typically will have greater than 80% transmittance and less than 30% haze.

The following are presently preferred LLDPE's.

Escorene LPX-2.04 from Exxon Chemical Company has an MI of 2.0; Density 0.918; Melting Point 121.5° C.; in thin films (1.25 mil) it has a haze of 26%; Ultimate Tensile Strength (UTS) (MD) 320 Kg/cm$^2$ (4500 psi), UTS (CD) 250 Kg/cm$^2$ (3500 psi).

Dowlex 2045 from Dow Chemical Company has an MI of 1.0; a density of 0.920; Vicat 100° C.; UTS (MD) 6500 psi, CD 5100 psi. Dowlex 2440 has an MI of 4.0; a density of 0.935; Vicat of 117° C.; and 18% haze.

Turning now to the selection of the second component, the styrene-ethylene-butylene-styrene (SEBS) will be characterized by terminal styrene blocks and central ethylene/butylene block in a linear chain. The present material may be further characterized and selected from other SEBS's currently available on the basis of several critical factors, one of which is the ratio of crystalline, rigidifying styrene component to rubbery middle block component, which will generally be in the range of 25-35/65-75. Another critical factor is that the SEBS be substantially free of additives, in that some SEBS materials comprise 25-50 wt% plasticizer oil. The present SEBS also has a tensile strength of 3000-5000 psi, ASTM 0412. Presently preferred SEBS materials are Kraton G 1650, tensile strength (ASTM D412), 5000, styrene/rubber ratio 28/72; 1651, tensile strength 3000, styrene/rubber ratio 33/67; and 1652, tensile strength 4500, styrene/rubber ratio 29/71. Kraton is a registered trademark of Shell Chemical Company.

The SEBS material used herein is further described in U.S. Pat. No. 3,595,942. It may be expected that other rubbery materials such as ehtylene propylene copolymer and ethylene propylene diene may be found suitable as well.

Turning now to the selection of the optional third component of a high melt index material, such a material will generally be a polyolefin so as to be compatible with the LLDPE and SEBS and have a melt index of 5-50. Presently preferred materials are Shell PP5820 polypropylene from Shell Chemical Co. and Escorene LPX-16 LLDPE with the following pertinent properties:

| Physical Property | ASTM Method | Shell PP5820 | Escorene LPX-16 |
|---|---|---|---|
| Melt Index, g/10 min | D1238E | — | 12 |
| Melt Flow, g/10 min | D1238L | 12 | — |
| Melting Point, °C. | — | 168 | 123 |

In other words, a relatively high MI and MP are desired. Also, a high elongation and other properties desirable in the first two components are desirable.

Acrawax-C ™ N, $N^1$ ethylene bis stearamide from Glyco chemicals, with 0.970 density and 140°-145° C. melting point range may be added in a conventional manner in up to 0.5% of the present blend to act as an antiblocking agent.

Finally up to 1% conventional antioxidants such as Anti-oxidant 330 from Ethyl Corp., 1,3,5-trimethyl-2,4,6-tris (3,5-ditertiary butyl-4-hydroxybenzyl) benzene may be used in the present blend.

EXAMPLE I

All percentages set forth in this specification are by weight, and all test methods are as set forth in this Example I.

49.9% LPX 2.04 LLDPE, 49.9% Kraton G 1652, and 0.2% Ethyl 330 antioxidant were dry blended in a ribbon blender at 30 rpm for 30 minutes, then extruded at 400±5° F. into a slot dies and calendered to obtain 7, 12, and 14 mil films in a 30 inch wide web with an extruder/calender machine which had a two stage screw with a mixing head. A homogenous blend was obtained to yield clear and flexible films. The films were subsequently formed into 1 liter rectangular pouches with an impulse sealer, and then filled with water, sealed at a relatively low temperature (270° F.) and sterilized at 115° C. for 30 minutes. Pouches were sterilized in this and subsequent Examples with over pressurization. This is, compressed air is introduced into the autoclave to prevent pressure in the pouch from rupturing the pouch, especially at the steam condensation point. The pouches maintained their integrity after vibrating at 240 cycles per minute with a 1 G force and being dropped from a 6 foot height. The material of Example I had a 0.43 MI and 76° C. Vicat softening point. The pouch shapes were maintained with 10% shrinkage. The 7 mil film was practically colorless, with thicker films having slight haze.

The shelf life of the foregoing blend has been calculated as 3.1 years for 12 mil film and 2.6 years for 7 mil film, based on time to 5% moisture loss.

This blend generally has excellent physical and chemical properties for a medicinal solution container, including minimum blushing; high flexibility; excellent elongation, in excess of any comparable material; and high impact strength. It may also be readily sealed to other materials, such as polypropylene, used in closures. The blend, however, has a relatively low MI and may beneficially be modified by addition of up to 10% of a third component such as polypropylene to produce a 45:45:10 blend.

EXAMPLE II 79.8% LPX 2.04 LLDPE, 20.0% Kraton G 1652 SEBS, and 0.2% Ethyl 330 anti-oxidant were dry blended in a ribbon blender for 30 minutes at 20 rpm, then transferred to an extruder/calender machine for melt homogenization with a 3.94 inch diameter screw having 5 feed flights, 5 transition flights, 8 metering flights, 3 flight lengths of mixing section, and a second stage of 3 metering flights. The extruder, with 24/1 L/D ratio and 4/1 compression ratio, fed the melted blend through a 39 inch wide slot die with 0.30 inch die gap into the nip of 260° F. calender rolls for subsequent roll release, cooling, edge trim slitting, and windup at 30 inch wide rolls with 0.007 inch and 0.012 inch gages.

The film had the following properties:

| Blend Properties | Test Method | Value |
| --- | --- | --- |
| Melt Index, g 10 min | ASTM D 1238-79 | 1.13 |
| Vicat Softening Point, °C. | ASTM D 1525-76 | 90 |

The 1 liter pouches maintained their shape and good clarity after sterilization at 115° C. and vibration (shipping) test film clarity measured 31% haze and 87% transmittance. Shrinkage was 7%. Greater than 10 drops from 6 feet were required to rupture the 0.012 inch gage pouches, while the 0.007 inch pouches maintained their integrity after 6 drops from 6 feet.

This blend retains the beneficial properties of the blend of Example I with the advantage of cost savings balanced against some loss in impact strength and heat resistance. Low temperature properties, barrier properties, and heat sealing properties are enhanced by higher amounts of LLDPE.

EXAMPLE III

50% LPX 2.04 LLDPE and 50% Kraton G 1650 were tumble blended and then pelletized in a 1¼ inch laboratory extruder, 24:1 LD ratio and a two stage screw with a mixing head. The next day the pellets were extruded into a 7 mil thick cast film.

The film looked clear and flexible, with a very slight haze and no color at all. The film had good tear strength and stretchability. The film could be easily heat sealed at 270° F.+10 psi air clamping pressure to give very strong seals. The film had excellent impact strength. Ports from the same or similar material could be easily sealed with an impulse, heat or ultrasonic sealer. The film had excellent strength and elongation. A one liter pouch filled with water was repeatedly dropped from 6 foot height without breaking.

Film according to Example III can be easily steam sterilized. An empty pouch with only air inside or water inside can be sterilized at a temperature up to 120° C. without excessive deformation, blocking or blushing. To be able to sterilize a bag in the empty condition or with only a small amount of liquid in it has particular significance for blood or pooling bag application. Some materials that block excessively are excluded from this type of use or may require special processing in the sterilizer to avoid blocking when hot.

BARRIER PROPERTIES 8 mil thick film has the following barrier properties as measured on a Mocon film permeability instrument from Modern Controls, Inc., Elk River, MN:

The $CO_2$ transmission was 5880 c.c./$M^2$/day at 1 atm., room temperature; and The $O_2$ transmission was 970 c.c./$M^2$/day at 1 atm., room temperature.

The Vicat softening point of the blend is 76° C.

Example III demonstrates a cast film with properties particularly desirable in a blood bag application as well as a solution container. For example, it can be sterilized empty and it has $CO_2$ and $O_2$ transmission approximately twice that of a standard DOP-plasticized PVC bag, allowing extended blood storage time.

EXAMPLE IV

60% LPX 2.04 and 40% Kraton G 1650 were weighed into a ribbon blender. To the blend, 0.5 PHR of anti-oxidant Ethyl 330 and 0.1 of Acrawax-C ™ were added and then ribbon blended at 20 RPM for 30 minutes. 10 pounds of this material were molded for ASTM test samples at 250° C. The other 10 pounds were pelletized by extruding through a laboratory twin screw extruder at 183° C. The next day the pellets were extruded through a single screw extruder at 209° C. into blown film of about 8 mil thickness in lay flat tube of 3 inch diameter.

The film had the following properties:

| Blend Properties | Test Method | | |
| --- | --- | --- | --- |
| Melt Index, g/10 min. | ASTM D 1238-79 | 0.62 | |
| M.P., °C. | DSC 75 | 115° C., 121° C. | |
| Vicat Softening Point, °C. | ASTM D 1525-76 | 84° C. | |
| Radiation Sterilization | | | |
| Injection Molded Samples | | Before | After |
| Tensile at Break, psi | ASTM D 638-77a | 1800 | 1924 |

| | -continued | | |
|---|---|---|---|
| | Test Method | | |
| Elongation, % | ASTM D 638-77a | 627 | 644 |
| Color | ASTM D 2849-69 | V. slight yellow | slight yellow |
| Low Temperature Brittleness | | | |
| Injection Molded Samples | ASTM D 746-79 | < −100° C. | |
| Film Pressouts | ASTM D 1790-62 | < −76° C. | |
| Heat Sealing Properties Film | | | |
| Impulse Sealing | | Excellent | |
| Thermal Bar Sealing | | Excellent | |
| Sonic Welding | | Excellent | |
| Color | | Colorless | |
| Strength Properties | | | |
| Injection Molded Samples (as molded) | | | |
| Tensile yield, psi | ASTM D 638-77a | 902 | |
| Elongation, % | ASTM D 638-77a | 627 | |
| Flexibility (Flex modulus) | | | |
| Injection Molded Samples | ASTM D 790-78 | 22 K | |

The film was clear and very flexible, with good tear resistance and excellent stretchability.

The lay flat tube was filled with 500 ml of water and sealed at both ends into pouches. The pouches were sterilized at 115° C. using 25 psi overpressure for 45 minutes. Very little shrinkage and blushing was observed. The pouches passed repeated (over 10) drop tests from six feet onto concrete.

An injection molded sample was exposed to 2.5 Megarad gamma radiation. It showed that, overall, the physical properties of the present blend are not significantly affected by radiation sterilization. Test results on other blends confirm this observation.

The low temperature brittleness data demonstrates the flexibility of this blend at low temperatures. These properties were also observed in connection with other blends, containing LPX 2.04 and 30% and 80% Kraton.

EXAMPLE V

62% LPX 2.04, 30% Kraton G 1650, and 8% Shell PP5820 (polypropylene) were ribbon blended with 0.5% Ethyl 330 Antioxidant and 0.1% Acrawax-C at 20 rpm for 30 minutes. 10 pounds were molded for test samples and 10 pounds were extrusion homogenized in a Haake TW-100 laboratory twin screw extruder with a single strand die and pelletized. The pellets were then re-extruded in a single screw extruder with a one inch blown film die to obtain a lay flat film tube of about 3 inch diameter.

The film was heat sealed at 270° F. and 10 psi to form 500 ml water-filled pouches. These were sterilized at 115° C. in a steam sterilizer using 27 psi overpressure followed by air cooling. All pouches survived sterilization without blushing and exhibited excellent clarity, stretchability, impact resistance, and tear resistance.

The pouches were then radiation sterilized by the method of Example V. Again, no significant loss of properties was observed.

The pouches were also tested for low temperature brittleness by the method of Example IV. Again, excellent low temperature properties were observed.

The film had the following properties:

| Melt Index, g/10 min. | 1.2 | |
|---|---|---|
| M.P., °C. DSC | 115, 121, 161 | |
| Vicat Softening Point, °C. | 92.6 | |
| Radiation Sterilization Injection Molded Samples | Before | After |
| Tensile at Break, psi | 2110 | 2207 |
| Elongation, % | 733 | 706 |
| Color | off white | very slightly yellow |
| Flex modulus psi | 25 K | 31 |
| Low Temperature Brittleness | | |
| Injection Molded Samples | < −100° C. | |
| Film Pressouts | < −76° C. | |
| Strength Properties Injection Molded Samples | | |
| Tensile, psi | 1136 | |
| Elongation, % | 733 | |

EXAMPLE VI

50% Dowlex 2440 and 50% Kraton G 1652 were blended in a ribbon blender at 20 RPM for 30 minutes, followed by melt blending on a two roll mill at 350° F. This blend was then heat pressed into a 15–20 mil film and an ASTM injection molded test sample and tested.

The heat pressed sheet looked soft and flexible with slight haze, with good tear resistance and stretchability.

5×10 inch pouches of this film with 1 liter of water were sterilized at 115° C. successfully. The film blushed, but exhibited no deformation. Sterilized bags easily pass six foot drop test. Excessive blushing makes this material unsuitable for an IV container but is useful for applications were clarity is not an issue, such as a blood bag, plasma pooling bag, etc.

This material had a Vicat softening point of 94° C.

This Example shows the use of a relatively higher density LLDPE to produce a material which, while still meeting accepted criteria for a medical solution container, represents a trade off of higher temperature resistance, lower clarity, and less impact resistance.

EXAMPLE VII

70% Dowlex 2045 and 30% Kraton G 1652 were tumble blended and homogenized on a 2 roll mill at 325° F., then pressed out at 320° F. under 10 psi for 1 minute into 0.015–0.020 inch sheets and ASTM test samples.

The film sheets looked soft and flexible with only very slight haze. The film had good tear resistance and excellent stretchability. The film can be easily heat sealed at 270° F. with 10 psi air pressure. Seals were good and very strong. The film had excellent impact strength. A 5"×12" one liter bag with water passed six foot drop tests repeatedly and consistently.

Pouches made from the sheets were sterilized at 115° C. successfully without excessive deformation or blushing.

The Vicat softening point of this blend is 78° C.

This Example shows the use of an LLDPE of a low molecular weight (low MI) with a low flexural modulus (38 K) and low yield strength (18 K psi) to produce a very flexible film with a high LLDPE content that is cost effective.

EXAMPLES VIII AND IX

A blend of 80% G 1650 and 20% Dowlex 2045 was formed into a blend but exhibited extremely low melt index and would not run on an extruder.

A blend of 90% LPX-2.04 and 10% Kraton G 1652 was blended, cast into film and formed into pouches. This material was found to have insufficient flexibility for impact testing.

These examples, taken in conjunction with those preceding, demonstrate the aspect of the present invention wherein superior desirable properties in a medical solution container are obtained through the use of LLDPE as a major component, i.e. 50 to approximately 90%.

EXAMPLE X

A film sample of 50% LPX-2.04 and 50% Kraton G 1650 was tested by extraction of 6000 cm$^2$/l with distilled H$_2$O at 70° C. for 24 hours. The extract was tested as follows: non-volatile residue 6.4 mg/l; oxidizable substances 0.4 mEq KMnO$_4$/l. This shows significant improvement over PVC plasticized with DEHP, which has typical test values of 0.2 mg/l non-volatile residue and 0.61 oxidizable substances.

MEDICAL SOLUTION CONTAINER

The flexible film material of the present invention may be manufactured by several processes and fabricated into several types of containers.

The presently preferred method of manufacture of the present film material is in the form of cast or blown film 5–20 mil thick created from dry blended resin components in commercially available equipment, as described in the preceding Examples. The present film material, however, may also be blow molded into flexible film containers from injection molded parisons utilizing commercially available blow molding equipment.

The presently preferred container is shown in FIG. 1. Illustrated therein is an autoclaved sterilized 250 ml container containing 50–100 ml of injectable fat emulsion, for parenteral application via a conventional non-vented I.V. administration set having flexible tubing, a patient delivery needle, and a spike for insertion into a container.

The container comprises two sheets of film 10, 12 which have been heat-sealed or impulse-sealed along two parallel sides 14, 16 and along a hanger end 18 as described hereinafter.

The hanger end 18 comprises an aperture 20, defined by the heat-sealed area so that the container may be hung from a conventional I.V. stand.

Figure 2:
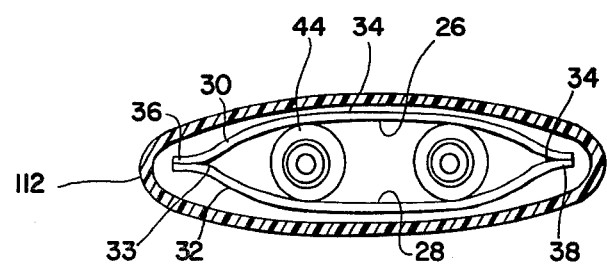
FIG. 2 is an end view of the container of FIG. 1.

Opposite the hanger end 18, and generally parallel thereto is a port end member 22 comprising a planar base portion 24 having a thickness of about 0.03 inch and being in the approximate shape of a hexagon with two parallel longer side portions 26, 28 parallel to the widths of the film sheets 10, 12 and, at each end, a pair of angled side portions 30, 32 joined in an acute angle at a sharp edge portion 33, as shown in FIG. 2. The planar base portion is continuously bounded at its edge by a flange portion 34 extending approximately one half inch above and below the base portion at right angles thereto. The flange portion thereby forms a continuous band around the base portion in the configuration of the base portion and provides a smooth, continuous surface having parallel sharp edges, as shown at 33, for bonding to the two film sheets 10, 12. The port end member 22 is inserted between the two film sheets, which have previously been joined on three sides, and heat sealed to the film by two shaped jaws. The film extends slightly beyond the length of the port end member in two ears 36, 38, whereat the film is joined to itself, the film layers each being continuously joined to the port end member along their intermediate portions between the ears to form a closed container ready to be filled.

The preferred method of filling the present container comprises the provision in a first heat sealing operation of two openings 40, 42 in the continuous heat seal across the hanger end. After the container has been formed, a fill tube is inserted into either of the two openings and solution is pumped into the container. The hanger end is then completely sealed in a second heat sealing operation which seals the two openings 40, 42.

The present blends have been found to be compatible with port end members made from commercially available polypropylene. The present blends may also themselves be readily injection molded into formed components disclosed herein, as well as tubing, etc.

Figure 3:
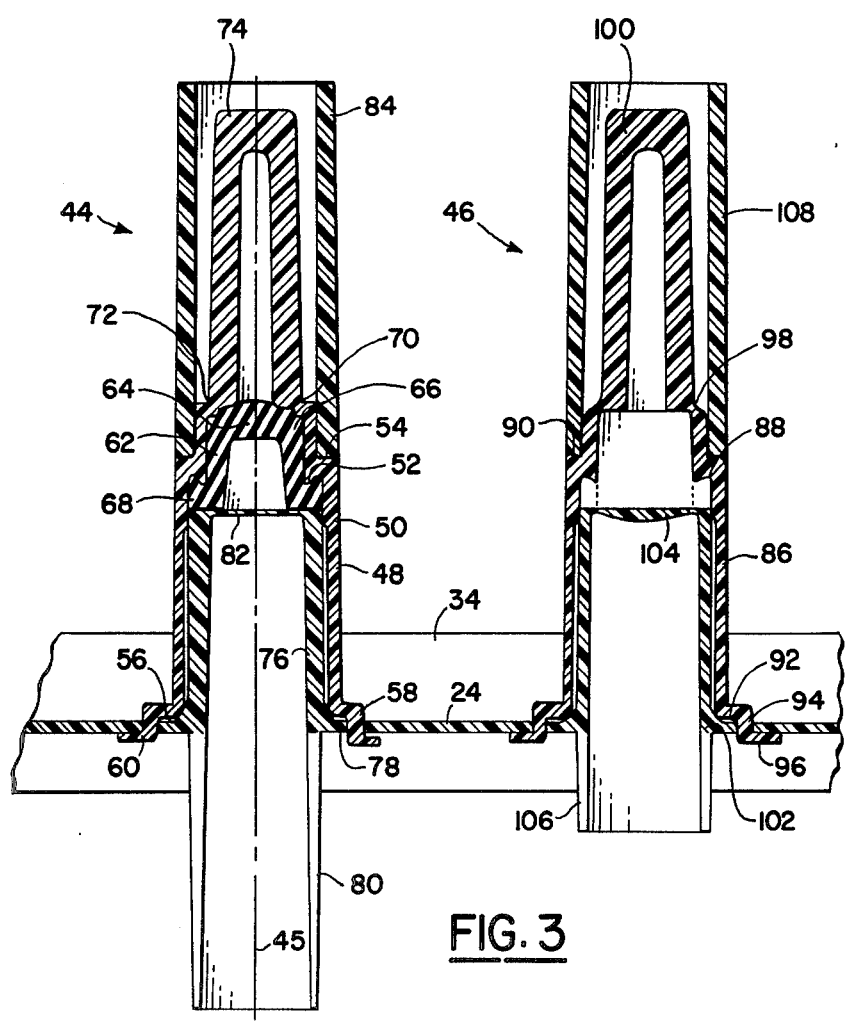
FIG. 3 is a detailed view of port structure of the container of FIG. 1.

The port end member 22 is provided with a pair of circular apertures in its base portion 24, through which extend first and second port assemblies 44, 46 for receiving a syringe needle and an administration set, respectively. These port assemblies are shown in detail in FIG. 3.

The first port assembly 44 extends generally in a cylindrical shape along a central axis 45 from inwardly of the container to outwardly of the container, as defined by base portion 24.

The first port assembly 44 comprises a stepped tubular member 48 extending from inside the planar base 24 to a closed, frangible tip section 74; a cylindrical diaphragm member 76 extending well inside the container and terminating in a diaphragm 82; a septum 62; and a port protector 84 surrounding the frangible tip.

The stepped tubular member 48 comprises a main cylindrical section 50 with a radially inwardly stepped portion 52 at a container-external axial end thereof, with the tubular portion thereabove being radially smaller to define an outer ledge portion 54 above the inwardly stepped portion 52. At its opposite end, the stepped tubular member 48 comprises a radially outwardly extending seat portion 56 terminating circumferentially in an axially extending lip 58 and a radially outwardly extending flange 60. The flange 60 is sonic-welded or otherwise joined to the base portion 24 on the container-internal side, the lip portion 58 extending in sealing relationship through an aperture in the base portion 24.

A rubber septum 62 is inserted into the tubular member 48 from the container-inward side. It comprises a disc portion 64, a cylindrical side portion 66 extending axially therefrom and a radially outwardly stepped portion 68 which seats against the stepped portion 52 of the tubular member 48. The disc portion 64 seats against a radially inwardly stepped portion 70 of the tubular member 48, which terminates radially inwardly in a thinned angular portion 72 curving sharply to a tapered, axially extending close-ended tubular portion 74 which serves as a cover for the rubber septum 62. In use, the closed tubular portion 74 may be snapped off along thinned angular portion 72 to expose the rubber septum 62 which provides a resealing closure when medicaments or the like are injected into the container through a hypodermic syringe.

A cylindrical diaphragm member 76 is next inserted into the assembly. It is generally cylindrical having a radially outwardly extending flange 78 in an intermediate portion which fits into the seat portion 56 of the stepped tubular member 48. The cylindrical diaphragm member 76 extends inwardly into the container in two segments, one being shown in FIG. 3 at 80. The diaphragm member terminates outwardly from the container in a thinned circular portion 82 extending across the stepped tubular member 48 and abutting the rubber septum 62 to hold the latter in place. The diaphragm can be easily penetrated by a syringe needle.

Finally, a port protector 84 is slipped over the frangible closed tubular portion 74 and seated on the outer ledge portion 54 of the stepped tubular member 48. The port protector 84 is generally in the configuration of an open-ended cylindrical tube and is slip fit or heat bonded onto the tubular member to provide a tamper-evident closure.

Referring now to the second port assembly 46, a spike port is provided thereby which uses substantially identical components as those described in connection with the first port assembly. A second stepped tubular member 86 is provided with a second stepped portion 88, outer ledge portion 90, seat portion 92, lip 94, and flange 96 as described in connection with the first stepped tubular member 48. The flange 96 is fixed to the base portion 24 of the port end member 22 in a similar manner. The second stepped tubular member 86 further comprises a thinned angular portion 98 curving sharply to a tapered, axially extending tubular portion 100 which serves as a port cover and may be snapped off as described in connection with the first tubular member 48.

A second inner diaphragm member 102 is formed and inserted in a manner substantially identical to that described in connection with the inner cylindrical diaphragm member 76. A thinned circular portion 104 of the second inner diaphragm member 102 serves as the primary inner closure in the second port assembly, there being no rubber septum, and is constructed to receive a spike in a conventional non-vented I.V. administration set. The inner segmented portion 106 of the second inner diaphragm member 104 does not extend to a container-internal direction to the extent of the segments of portion 80 of the first inner diaphragm member since the first segments protect against needle puncture of the bag, and the second segments serve to receive and grip the spike. The segments, extending to the base 24 of the hanger end member, provide complete emptying of the bag when it is hung from the hanger end.

A second port protector 108, substantially identical to the first-described port protector 84 is slip fit or otherwise affixed to the second stepped tubular member 86 to prevent accidental breaking of the frangible section and to permit easy removal of the port protector.

Although the present material has been described in connection with an intravenous solution container, it is also been found useful in forming a conventional blood bag. The film material, as discussed in connection with the foregoing examples, has excellent low temperature properties, which are important for blood bags used to produce cryoprecipitates and the like. The film material also may be fabricated with a high degree of gas transmission, which is vital to platelet survival.

Finally, it should be noted that the film material may be useful in a container for fat emulsion. It is particularly advantageous for this application due to its extremely low level of fat-soluble extractable materials. PVC, in contrast, contains plasticizers and trace ingredients which make it unsuitable as a fat emulsion container. As used in a fat emulsion, the present material may be fabricated as described in connection with FIGS. 1-3, and a foil laminate overwrap used to enclose the container to prevent gas permeation from damaging the fat emulsion. An air impermeable overwrap 112 is shown diagramatically in FIG. 2, and simply consists of a completely enclosed, sealed pouch which contains the film bag. The pouch is preferably flushed with nitrogen prior to sealing. The pouch may be formed of 2-10 mil thick films of polymeraluminum foil laminate with suitable antiblock. The blends of the present invention exhibit very high $CO_2$ and $O_2$ permeability which may damage certain solutions such as fat emulsions. It may therefore also be desirable to fabricate a container using the present material wherein the overwrap is formed by a laminate construction with an air-impermeable layer.

What is claimed is:

1. A flexible film material, comprising:
   (a) a first component of 30-90% linear low density polyethylene material having a density of 0.918-0.940 g/cm³ and a melting point less than 125° C.;
   (b) a second component of 10-70% of styrene-ethylenebutylene-styrene block copolymer;
   (c) said components being selected and proportioned so that a flexible film container may be manufactured therefrom and sterilized at temperatures up to 120° C.

2. A container formed from material as defined in claim 1, comprising a spike port, a medicinal entry port, and an air impermeable overwrap.

3. The container of claim 2 wherein said spike port and medicinal entry port are formed of essentially the same material as the film material.

4. The material of claim 1 wherein said first component makes up 70-80% of said film.

5. The material of claim 1 wherein said second component makes up 20-50% of said film.

6. The material of claim 6 wherein said first component has a Vicat softening point in excess of 90° C.

7. A flexible film material consisting essentially of:
   (a) a first component of 30-90% linear low density polyethylene material having a density of 0.918-0.940 g/cm³ and a melting point less than 125° C.;
   (b) a second component of 10-70% of styrene-ethylene-butylene-styrene block copolymer; and
   (c) a third component of 1-10% of polyolefin having an MI of 5-50, being heat sterilizable at temperatures up to 120° C.

8. The material of claim 7 wherein said first component makes up 45-62% of said film material.

9. The material of claim 7 wherein said second component makes up 20-50% of said film material.

10. A container formed from the material of claim 1, comprising a spike port, a medicinal entry port, and an air impermeable overwrap.

11. The material of claim 7 wherein said first component is further characterized by a melt index of 0.1 –5.

12. The material of claim 7 wherein said third component is linear low density polyethylene.

13. The material of claim 7 wherein said third component is polypropylene.

14. A flexible film material consisting essentially of:

(a) a first component of linear low density polyethylene having a density of 0.918–0.940 g/cm$^3$ and a melting point of less than 125° C.;
(b) a second component of styrene-ethylene-butylene-styrene block copolymer being substantially free of additives and having a styrene to rubber ratio of 25–35/65–75; and
(c) 0–10% of a third component having a melt index of 5–50 and selected from the group consisting of linear low density polyethylene and polypropylene.

* * * * *